(12) United States Patent
Li

(10) Patent No.: US 10,881,485 B2
(45) Date of Patent: Jan. 5, 2021

(54) SYSTEM FOR PROVIDING ENDODONTIC MATERIAL USING INDUCTION HEATING

(71) Applicant: Tulsa Dental Products LLC, Tulsa, OK (US)

(72) Inventor: Nathan Y. Li, Mailbu, CA (US)

(73) Assignee: DENTSPLY SIRONA INC., York, PA (US)

( * ) Notice: Subject to any disclaimer, the term of this patent is extended or adjusted under 35 U.S.C. 154(b) by 68 days.

(21) Appl. No.: 15/700,989

(22) Filed: Sep. 11, 2017

(65) Prior Publication Data
US 2018/0085196 A1   Mar. 29, 2018

Related U.S. Application Data

(60) Provisional application No. 62/393,029, filed on Sep. 11, 2016, provisional application No. 62/393,030, filed on Sep. 11, 2016.

(51) Int. Cl.
*A61C 5/55* (2017.01)
*A61C 5/62* (2017.01)
(Continued)

(52) U.S. Cl.
CPC .............. *A61C 5/55* (2017.02); *A61C 1/0015* (2013.01); *A61C 5/62* (2017.02); *A61C 5/66* (2017.02);
(Continued)

(58) Field of Classification Search
CPC .... A61C 5/55; A61C 5/66; A61C 5/62; A61C 1/0015; A61K 6/0038; H05B 6/06; H05B 6/105
See application file for complete search history.

(56) References Cited

U.S. PATENT DOCUMENTS

D223,596 S  *  5/1972  Courtenay ............... A61C 5/64
                                                     D24/127
3,917,062 A    11/1975  Winters
(Continued)

FOREIGN PATENT DOCUMENTS

WO    20130141564 A1    9/2013

OTHER PUBLICATIONS

International Search Report; PCT/US2017050974; Mar. 14, 2018 (completed); dated Apr. 6, 2018.
(Continued)

*Primary Examiner* — Cris L. Rodriguez
*Assistant Examiner* — Hao D Mai
(74) *Attorney, Agent, or Firm* — Dentsply Sirona Inc.

(57) ABSTRACT

A system for providing endodontic material includes an application device and a docking station for the application device. The application device includes a cartridge having a chamber structure containing endodontic material, with the chamber structure capable of being heated by magnetic induction. The application device also includes a handle assembly configured to hold the cartridge. The docking station includes a slot configured to contain the application device with a part of the application device positioned in the slot. The docking station is provided with an induction heating coil positioned adjacent to the slot, with the induction heating slot being configured to heat the cartridge of the application device.

13 Claims, 5 Drawing Sheets

(51) Int. Cl.
*A61C 5/66* (2017.01)
*A61K 6/54* (2020.01)
*A61C 1/00* (2006.01)
*H05B 6/06* (2006.01)
*H05B 6/10* (2006.01)
*H05B 6/38* (2006.01)

(52) U.S. Cl.
CPC .............. *A61K 6/54* (2020.01); *H05B 6/06* (2013.01); *H05B 6/105* (2013.01); *H05B 6/38* (2013.01)

(56) References Cited

U.S. PATENT DOCUMENTS

| | | | | |
|---|---|---|---|---|
| 4,382,788 A * | 5/1983 | Pelerin | ............... | A61C 5/44 422/300 |
| 5,006,066 A * | 4/1991 | Rouse | ............... | A61C 3/04 206/369 |
| 5,071,346 A * | 12/1991 | Domaas | ............... | A61C 3/04 206/369 |
| 5,154,611 A * | 10/1992 | Calvin | ............... | A61C 5/42 206/369 |
| 5,172,810 A * | 12/1992 | Brewer | ............... | A61C 3/04 206/368 |
| 5,328,367 A * | 7/1994 | Johnson | ............... | A61C 5/50 433/224 |
| 5,372,759 A * | 12/1994 | Johnson | ............ | A61C 13/0028 264/16 |
| 5,382,161 A * | 1/1995 | Roane | ............... | A61C 5/50 433/224 |
| 5,435,979 A * | 7/1995 | Miller | ............... | A61C 3/04 206/369 |
| 5,464,348 A * | 11/1995 | Fischer | ............... | A61C 19/10 206/369 |
| 5,525,314 A * | 6/1996 | Hurson | ............... | A61C 3/04 206/369 |
| 5,626,227 A * | 5/1997 | Wagner | ............... | A61C 3/04 206/369 |
| 5,743,734 A * | 4/1998 | Heath | ............... | A61C 3/04 206/369 |
| 5,967,778 A * | 10/1999 | Riitano | ............... | A61C 19/002 206/366 |
| 6,236,020 B1 * | 5/2001 | Friedman | ............... | A61C 19/00 219/385 |
| 6,252,202 B1 * | 6/2001 | Zychek | ............... | F27B 17/025 219/385 |
| 6,681,925 B2 * | 1/2004 | Fischer | ............... | A61C 19/02 206/369 |
| 7,195,485 B2 * | 3/2007 | Fischer | ............... | A61C 5/42 206/369 |
| 7,278,852 B2 * | 10/2007 | Fischer | ............... | A61C 5/42 206/63.5 |
| 2005/0170313 A1 | 8/2005 | Pitz | | |
| 2008/0187883 A1 | 8/2008 | Lee | | |
| 2011/0165537 A1 * | 7/2011 | Jung | ............... | A61C 5/55 433/32 |
| 2013/0037570 A1 * | 2/2013 | Broyles | ............... | A61C 5/64 222/137 |
| 2013/0122450 A1 * | 5/2013 | Simons | ............... | A61C 5/55 433/27 |
| 2013/0122451 A1 * | 5/2013 | Simons | ............... | A61C 5/55 433/27 |
| 2013/0122452 A1 * | 5/2013 | Simons | ............... | A61C 5/55 433/27 |
| 2013/0122455 A1 * | 5/2013 | Simons | ............... | A61C 5/55 433/32 |
| 2013/0149664 A1 | 6/2013 | San Miguel | | |
| 2013/0175300 A1 | 7/2013 | Gyakushi | | |
| 2013/0230821 A1 * | 9/2013 | Brown | ............... | A61C 5/55 433/29 |
| 2014/0349244 A1 | 11/2014 | Patel | | |
| 2015/0079538 A1 | 3/2015 | Li | | |
| 2015/0188023 A1 * | 7/2015 | Pond | ............... | A61C 1/07 433/86 |
| 2018/0214247 A1 * | 8/2018 | Sharma | ............... | A61C 5/50 |

OTHER PUBLICATIONS

Written Opinion of the International Searching Authority; PCT/US2017050974; Mar. 14, 2018 (completed); dated Apr. 6, 2018.
International Preliminary Report on Patentability; PCT/US2017050974; Mar. 14, 2018 (completed); dated Apr. 6, 2018.

* cited by examiner

SYSTEM FOR PROVIDING ENDODONTIC MATERIAL USING INDUCTION HEATING

This application claims priority to U.S. Provisional Application Nos. 62/393,029 and 62/393,030, both of which were filed on Sep. 11, 2016, and both of which are incorporated by reference in their entirety.

BACKGROUND

Field of the Invention

This invention is related to a system that provides endodontic material for use in a dental procedure, with the system using inductive heating to heat the endodontic material. In particular, this invention is related to a system for providing endodontic material that includes a docking station and an endodontic material application device that have inductive heating elements for heating endodontic material, such as gutta percha, contained in the application device.

Related Art

Dental root canal treatments are a type of endodontics that are performed to remove infected dental pulp tissue inside the pulp chamber and root canals. After the infected dental pulp is removed, the vacant space is filled with an endodontic material. The ultimate objective of root canal treatment is to eliminate the infection inside the dental root system and to tightly seal or obturate, in three dimensions, the tiny openings at the end of the root canal (referred in the art as an apex). Dental root canal treatment therefore generally involves three stages: shaping, cleaning, and obturation (i.e., filling and sealing). Failure to completely seal the apex or the root canal in three dimensions leads to micro-leakage, which will lead to future bacteria colonization inside the root canal system, re-infection, and possible loss of the tooth. Indeed, micro-leakage is the most common cause of tooth failure.

The filling of the cleaned and shaped root canal space has been traditionally undertaken with a low-thermo endodontic compound, most often dental gutta percha. Previously, root canal treatment processes involved placement of the root canal filling and/or a sealing point or cone in a prepared root canal to plug the root canal, ideally in a manner to eliminate micro-leakage. However, conventional filling points and the process of application do not lend themselves well to providing a good seal of the root canal apex.

A popular method to apply dental root canal filling material into root canal space is warm gutta percha technique. Part of this technique is to preheat and soften gutta percha material, and then inject the softened gutta percha material into root canal space through a fine needle. Currently there different types of application devices for performing warm gutta percha technique. One such application device is similar to a conventional glue gun. This type of device has a heating barrel that is part of the gun-shaped applicator. An operator puts a piece of cylindrical rod shaped gutta percha into the heating chamber and attaches a fine needle in front of the barrel. After activating the heating element in the gun barrel to soften the gutta percha material, the dentist pulls a trigger to push a piston rod into the heated gun barrel, so as to squeeze the softened gutta percha material through the fine needle into the prepared root canal in the patient. However, since the gutta percha rod is directly inserted into heating chamber and softened before being dispensed, it leaves quite a sticky residue in the chamber. The residue must be cleaned with chemicals to prepare the application device for the next use. But the vapor from the cleaning chemicals might be harmful to, for example, expected mothers. Further, cross contamination among patients is a risk.

Other types of application devices have been designed to address some of the problems associated with the glue gun type devices. For example, some devices use gutta percha rods encased in disposable metal cartridges. Such cartridges generally have diameters of about 2.8 to 3.0 mm and are about 18 mm long. Ends of cartridges are connected to fine needles, and the other ends of the cartridges have a small nylon ball or pellet to seal off the end. Instead of a mechanical trigger configuration in the first type of applicator devices, the second type of applicator devices has a micro motor to move a piston forward to push gutta percha material out through the needle. This type of device is easier to clean, as the cartridge containing the gutta percha material is disposable.

The heating elements in both of the above-described types of devices share a common design, with heating pads and/or heating coils located on the body of the heating barrel. This heating element design can be problematic in in-vivo clinical applications. For example, with the placement of the heating coils on the body of the heating barrel, the barrel is bulky. It can therefore sometimes be hard to use the device to reach the back molar area of a patient's mouth. Another problem is that the heating mechanism might not be efficient because there may be air space between the endodontic material and the heating element provided in the heating chamber of the device. In this regard, gutta percha endodontic material generally needs to be heated to about 90° C. to about 125° C. in order to become soft enough to easily flow from the device. But, an operator will often need to set the device to heat to a much greater temperature in order to have sufficient heat transferred from the heating element to the cartridge containing the gutta percha. And the higher operating temperature can cause problems. For example, there is an increased risk of burning a patient when using the hot device. Thus, a thermo-protective sleeve is often used around the device body to protect the patient, with the sleeve in turn making the device even bulkier and difficult to maneuver. Moreover, given that the heating element in the application devices must be able to provide heat at higher temperature, the heating mechanism takes up more space, which further adds to the overall size of the device. Another problem is the heat transfer from the heating elements to the endodontic material is not consistent given the air space between the endodontic material and the heating chamber is not always consistent. In the event of excessive heat transfer, the endodontic material can become overheated and liquefy, causing the endodontic material to run off and possibly flow out of the needle before the operator is ready to use the device.

It is therefore desirable to develop a warm endodontic material application device that overcomes the drawbacks of the previous devices.

It is therefore desirable to develop a warm gutta percha applicator system that overcomes the drawbacks of the previous systems.

SUMMARY OF THE INVENTION

According to one aspect, the invention provides a system for providing endodontic material. The system includes an application device having a cartridge with a chamber structure containing endodontic material, and with the chamber structure capable of being heated by magnetic induction. The application device also includes a handle assembly configured to hold the cartridge. The system also includes a docking station including a slot configured to contain the application device with a part of the application device positioned in the slot, with the docking station being provided with at least one induction heating coil positioned adjacent to the slot.

According to another aspect, the invention provides a cartridge having a chamber structure configured to contain endodontic material. The cartridge also includes an outer sleeve configured to surround at least part of the chamber structure, with the outer sleeve including a slot extending through the sleeve that allows a portion of the chamber structure to be viewed through outer sleeve.

DETAILED DESCRIPTION OF THE INVENTION

This invention is related to a system for providing endodontic material that includes a docking station and an endodontic material application device that have inductive heating elements for heating endodontic material contained in the application device. In the descriptions herein, systems, devices, and methods will be described as being used in conjunction with an endodontic material, particularly gutta percha. These descriptions, however, should be understood as being merely exemplary. Indeed, as will be readily apparent to those skilled in the art the devices, systems, and methods described herein could be used to apply other materials, including non-endodontic materials.

Figure 1:
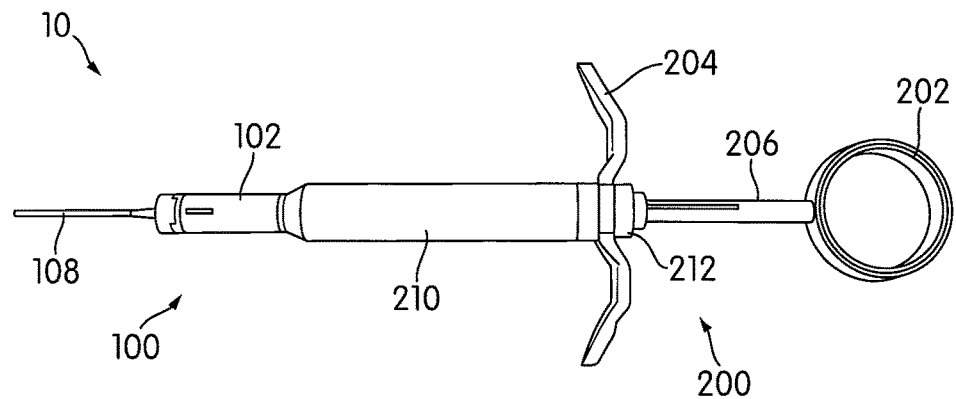
FIG. 1 is a view of an endodontic material application device according to an embodiment of the invention.
Figure 2:
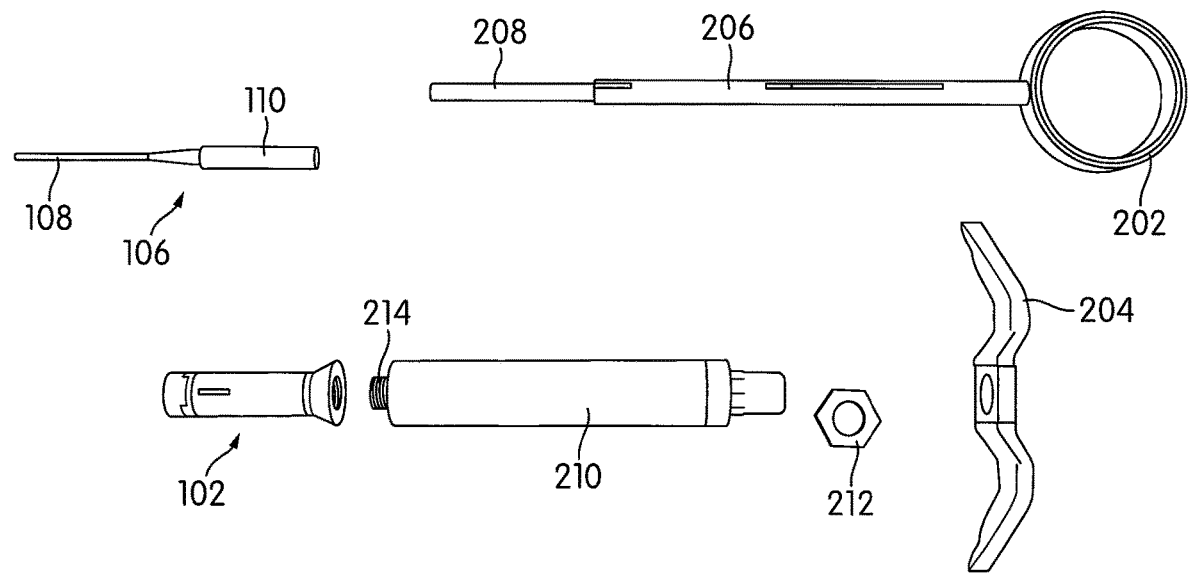
FIG. 2 is a view of parts of the endodontic material application device shown in FIG. 1.

FIGS. 1 and 2 are views of parts of an endodontic material application device 10. In this embodiment, the application device 10 is configured similar to a syringe. The application device 10 includes a cartridge 100 mounted to the handle assembly 200. The handle assembly 200 includes parts to be gripped by a user, including a thumb ring 202 and a finger grip 204. The thumb ring 202 is connected to one end of a push rod 206. At the other end of the push rod 206 is a plunger 208. The finger grip 204 and the push rod 206 are attached to a syringe body 210 with a locking nut 212. When the application device is used, the push rod 206 is pushed along the inside of the syringe body 210 such that the plunger 208 extends into the cartridge 100 and acts to force the endodontic material out of the cartridge 100, as will be described below.

As will be apparent to those skilled in the art, handle assemblies different than the specific handle assembly 200 shown in FIGS. 1 and 2 could be used with the invention described herein. In this regard, the only functionality required for the handle assembly be that it facilitate the dispensing of the endodontic material from cartridges as described herein. As an alternative to the depicted embodiment, the handle assembly could, for example, have a grip that is squeezed by the user to cause the movement of the push rod that forces the endodontic material out of the cartridge. Such a grip is shown in U.S. Patent Application Pub. No. 2015/0079538 A1, the disclosure of which is incorporated by reference in its entirety. In other embodiments, rather than using a force generated by the user, the handle assembly includes a motor that moves the push rod to thereby force the endodontic material out of cartridges. Such a motor could be a stepper type motor, with the stepper motor including gear teeth that mate with grooves provided on the push rod 206 to move the push rod 206 when the motor is powered on. An example of such a stepper motor is a piezo-electric motor, which is a small and energy efficient assembly capable of outputting power for use in forcing the endodontic material out of cartridges as described herein. In embodiments with a motor, the motor can be powered by a battery provided in the handle assembly, or the handle assembly can be provided with wiring to provide power to the piezo-electric motor.

Figure 3:
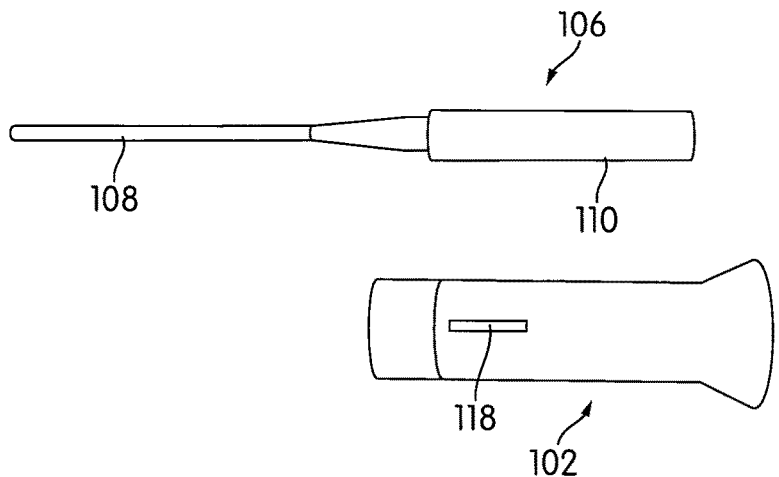
FIG. 3 is a view of parts of an endodontic material cartridge according to an embodiment of the invention.
Figure 4:
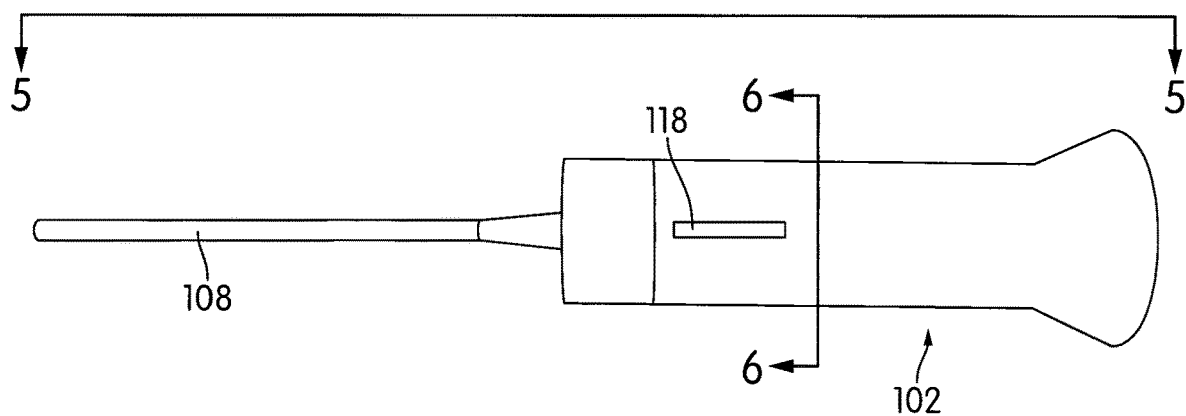
FIG. 4 is a side view of an endodontic material cartridge according to an embodiment of the invention.
Figure 5:
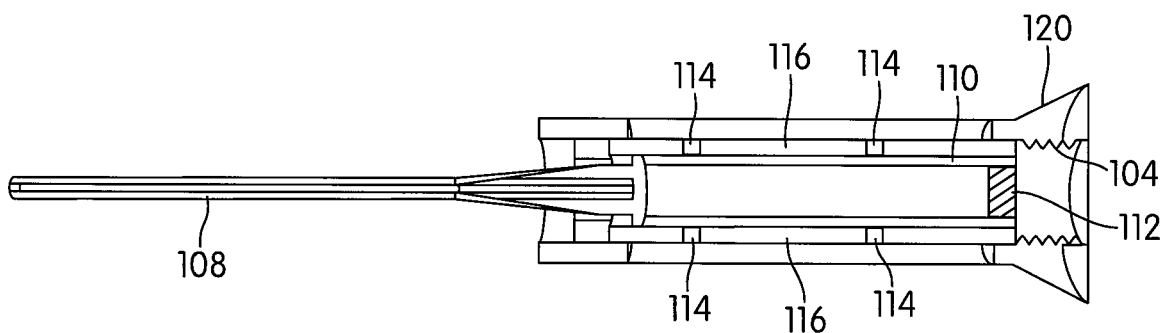
FIG. 5 is a cross-sectional view of the endodontic material cartridge shown in FIG. 4 as taken along the line 5-5.

FIGS. 3-5 show details of the cartridge 100. The cartridge 100 includes an outer sleeve 102, one end of which is attached to the syringe body 210. Specifically, one end of the sleeve 102 has screw threads 104 that receive a screw 214 provided at the end of the syringe body 210. In other embodiments, however, different structures can be used to connect the cartridge 100 to the syringe body 210, such as a snap-connecting structure. In still other embodiments, the end of the sleeve 102 is simply made to tightly fit over the outer surface of the end of the syringe body 210, or vice-versa. The sleeve 102 may be formed from, for example, a plastic material such that the sleeve 102 is not heated through when other parts of the cartridge 100 are heated through induction, as described below. In this regard, the sleeve 102 can be made from a variety of materials that are not susceptible to induction heating. An example of such a plastic material is ZYTEL® HTN92G45DH2, which is a polyamide resin with glass filler beads made by E. I. du Pont de Nemours and Company of Willington, Del.

The cartridge 100 also includes an endodontic material unit 106, which includes a chamber structure 110 for holding the endodontic material to be dispensed through a needle 108 that extends from the chamber structure 110. The needle 108 can be attached to the chamber structure 110 by a threaded joint, welding, gluing, or other suitable attachment means. A part of endodontic material unit 106 including the chamber structure 110 is positioned within the sleeve 102, with the needle 108 extending from the end of the sleeve 102. A sealing structure 112 (sometimes referred to as a ball seal) is movably provided within the chamber structure 110. The endodontic material is thereby sealed within the chamber structure 110 between the needle 108 and the sealing structure 112. When the application device 110 is used, the plunger 208 of the handle assembly 200 pushes the sealing structure 112 towards the needle 108 end of the cartridge 100, and the sealing structure 112 thereby functions as a piston that pushes the endodontic material out of the cartridge 100 through the needle 108.

In embodiments of the invention, the chamber structure 110 containing the endodontic material is formed from a magnetic material that is capable of being inductively heated. For example, the chamber structure 110 can be formed from a ferromagnetic metal alloy material such as nickel, cobalt, or stainless steel. In a particular embodiment, the chamber structure 110 is formed from 300 series stainless steel. By being formed from a ferromagnetic metal alloy, the chamber structure 110 can be heated in a magnetic induction field, as will be described below. It should be noted that because the chamber structure 110 can be heated by induction, unlike conventional heated endodontic material cartridges, an endodontic material cartridge according to the invention does not include any parts for electrically generating heat. For example, the cartridge 100 does not include a heating coil and electrodes connecting the heating coil to a power source. In other words, the chamber structure 110 itself becomes heat source. This is advantageous for multiple reasons. First, the chamber structure 110 is in contact with the endodontic material, thus, the endodontic material is efficiently heated in the cartridge 100. Second, as the cartridge 100 does not include electrical components, no electrical components will be inserted into the patient's mouth when the cartridge 100 is used in a dental procedure.

Figure 6:
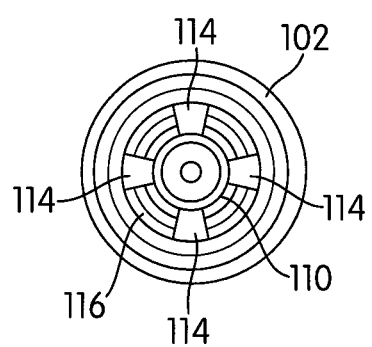
FIG. 6 is a cross-sectional view of the endodontic material cartridge shown in FIG. 4 as taken along the line 6-6.

As shown in the cross-sectional views of the cartridge 100 in FIGS. 5 and 6, the chamber structure 110 is spaced from the sleeve 102 by spacing pegs 114 that extend between the outer surface of the chamber structure 110 and the inner surface of the sleeve 102. An air gap 116 is thereby formed between the outer surface of the chamber structure 110 and the sleeve 102. The air gap 116 is highly effective thermal insulation between the chamber structure 110 and the sleeve 102. Thus, when the chamber structure 110 is inductively heated to soften the endodontic material (as discussed below), the air gap 116 insulation will prevent the sleeve 102 from being substantially heated. This is significant as the sleeve 102 may come into contact with a patient's mouth when the application device 10 is used in a dental procedure, which could cause a burn if the sleeve 102 is too hot.

The cartridge 100 with the needle 108, chamber structure 110, and the sleeve 102 may be disposable after the endodontic material is dispensed from the cartridge 100. Hence, the handle assembly 200 can be used with another cartridge. It should be noted, however, that while the combination of the needle 108, chamber structure 110, and the sleeve 102 are referred to herein as a "cartridge," in other embodiments different combinations of these and other structures can be combined to be used as cartridges for each use with other structures being reusable with the application device 10. For example, in an alternative embodiment, the chamber structure 110 and the needle 108 are provided together as a disposable unit (i.e., a "cartridge"), while the sleeve 102 is a reusable part of the application device 10. In such an embodiment, the chamber structure 110 and the needle 108 are made easily detachable from the sleeve 102. In another embodiment, the needle 108 and the sleeve 120 are made easily detachable from the chamber structure 110 such that the needle 108 and sleeve 102 are reusable parts of the application device 10, while the chamber structure 110 is a disposable part (i.e., a "cartridge").

Figure 7:
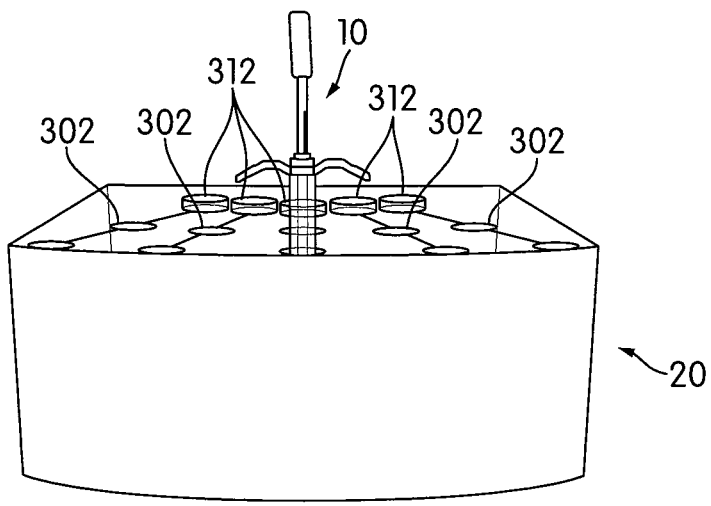
FIG. 7 is a view of a docking station with an endodontic material application device according to an embodiment of the invention.
Figure 8:
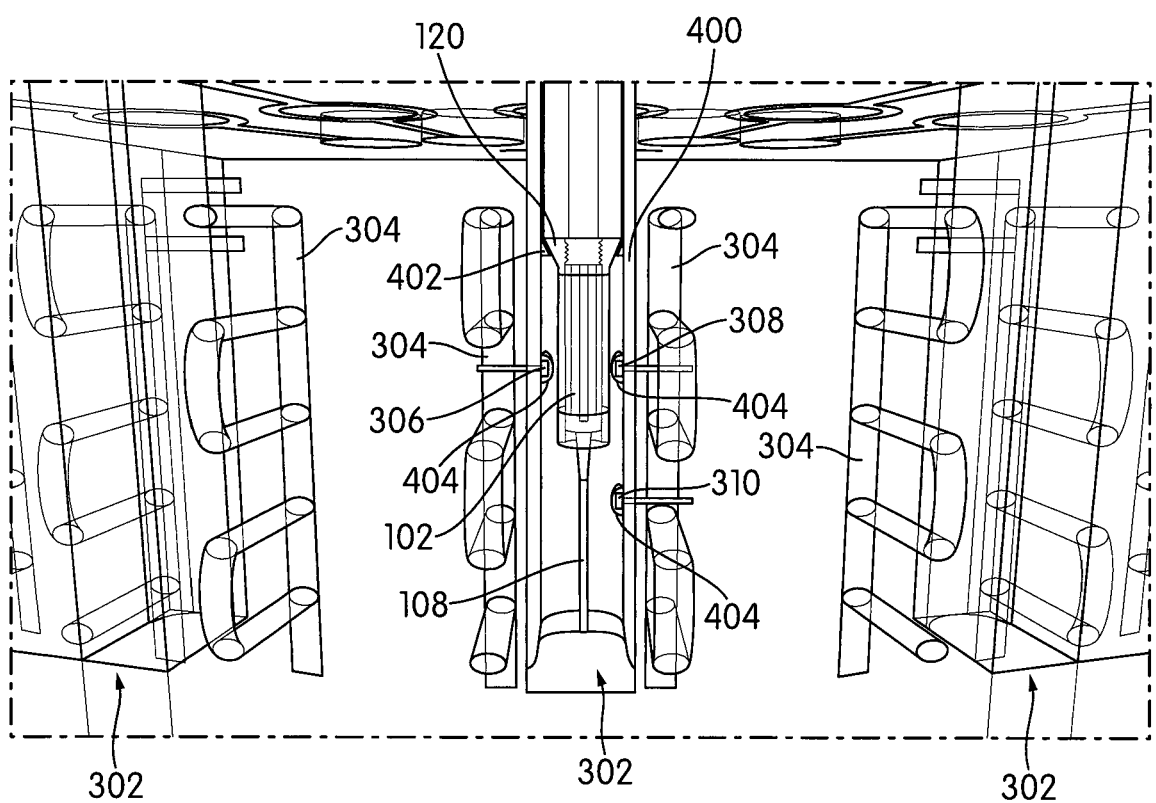
FIG. 8 is a view of the inside of the docking station shown in FIG. 7.

Referring to FIGS. 7 and 8, a docking station 20 for use with an application device 10 is shown. Together, the docking station 20 and the application device 10 form a system for providing endodontic material for use in a dental procedure according to an embodiment of the invention. The docking station 20 includes a slot 302 into which the side of the application device 10 with the cartridge 100 is inserted. The docking station 20 also includes additional slots 302 into which additional application devices can be inserted. In other embodiments, however, the docking station 20 only includes a single slot 302 for the application device 10.

FIG. 8 is a view of part of the inside of the docking station 20. Note that for convenience, many parts of the docking station have been omitted. As shown in the figure, inductive heating coils 304 are provided adjacent to the slot 302. More specifically, one coil 304 is provided adjacent to one side of the slot 302, and another coil 304 is provided adjacent to another side of the slot 302. The heating coils 304 are formed from an inductive heating material, such as copper. As discussed above, the chamber structure 110 in the cartridge 100 of the application device 10 is constructed from a magnetic material capable of being inductively heated in a magnetic field. Thus, when the inductive heating coils 304 are activated, the coils 304 generate a magnetic field that causes inductive heat generation in the chamber structure 110. The heat in turn will raise the temperature of the endodontic material contained within the chamber structure 110, thereby softening the endodontic material. The softened endodontic material can then be easily be forced out of the cartridge 100 when the application device 10 is removed the docking station 20 and the device is actuated by the user performing a dental procedure. As will be appreciated by those skilled in the art, with the configuration of the application device 10 and docking station 20, the induction heating to soften the endodontic material in the cartridge 100 can be done very quickly. For example, when the endodontic material is gutta percha, the chamber structure 110 may reach a sufficiently high temperature to soften the gutta percha in a matter of seconds after the induction heating is started.

In the embodiment depicted in FIG. 8, two induction heating coils 304 are provided for each slot 302, with the coils 304 having a generally flat shape. Such a configuration of induction heating coils 304 provides for fast and effective inductive heating of the cartridge 100 in the application device 10. In other embodiments, however, the induction heating coils can have configurations that are different from those shown in the figures. For example, a tubular induction heating coil could be used to surround the slots 302. Also, in the depicted embodiment the coils 304 are positioned adjacent to both section of the cartridge 100 with the chamber structure 110 and the needle 108. Thus, when the needle 108 is made from a magnetic material, the needle 108 will also become heated through induction. This can be advantageous in that the heated needle 108 will act to heat the endodontic material as it passes through the needle 108, and the endodontic material will thereby be easily maintained in a softened state as it passes through the needle 108. In other embodiments, however, the docking station 20 is modified such that a heating coil is not positioned adjacent to the needle 108, and thus, the needle 108 is not inductively heated in the docking station. Not inductively heating the needle 108 can be advantageous inasmuch as the unheated needle 108 will not cause a burn if the operator accidently contacts the patient's mouth. In sum, the heating of the application device 10 can be adapted for needs of a particular procedure.

To activate the coils 304, a power supply (not shown) can be provided in the docking station 10 and connected to the induction heating coils 304. An example of such a power supply is a zero voltage switching (ZVS) induction heating power supply module. More specifically, a ZVS power supply module used with the docking station 20 can have a power range from about 80 to 350 Watts. While such a power supply is effective in the docking station 20, those skilled in the art will also recognize other types of power supply modules that can be used in conjunction with the induction heating coils 304 in the docking station 20.

As shown in FIG. 8, the docking station 20 includes temperature sensors 306 and 308 facing the sleeve 102 of the cartridge 100. The temperature sensors 306 and 308 are configured to detect the temperature of the chamber structure 110 inside of the cartridge 100. To facilitate detection of this temperature, as shown in FIGS. 3 and 4 the sleeve 102 of the cartridge 100 includes slots 118 that allow the outer surface of the chamber structure 110 to be visible from outside of the sleeve 102. In other words, the slots 118 form windows to the chamber structure 110. The temperature sensors 306 and 308 in the docking station 20 are aimed at the slots 118, and thus can detect a temperature of the chamber structure 110. The temperature sensors 306 are connected to a control module (not shown) of the docking station 20, with the control module also being connected to the induction heating power supply. The temperature sensors 306 and 308 can thereby detect the temperature of the chamber structure 110, and relay that temperature to the control module. The control module in turn can control the heating power supply such that the induction heating coils 304 are turned on or off depending on whether the chamber structure 110 has reached a desired temperature. In a particular embodiment, the control module will use the highest temperature reading of the sensors 306 and 308 as the basis for controlling the coils 304. Notably, such a control system with the inductive heating coils can function on a millisecond time scale to provide for precise temperature control that would not be possible with conventional resistive heating cartridges, which often have a lagging peak and valley effect when their temperature is adjusted.

Those skilled in the art will recognize the variety of types of sensors that can be used as the temperature sensors 306 and 308 in the docking station 20. In some embodiments, the temperature sensors 306 and 308 are infrared (IR) temperature sensors. In other embodiments, the temperature sensors 306 and 308 are optical sensors (i.e., sensors configured to detect optical wavelengths of light). In embodiments with optical sensors, the outer surface of the chamber structure 110 can be provided with a thermo-reactive color strip at a position facing the slots 118 in the sleeve 102. The optical sensors 306 and 308 can thereby determine the temperature of the chamber structure 110 by reading the thermo-reactive color strip. Note, such a thermo-reactive color strip could be one-directional, and thereby indicating when the chamber structure 110 has reached certain temperatures, or the thermo-reactive color strip could be a reversible two-directional strip in which the color of the strip changes as the temperature of the chamber structure 110 rises and falls.

In the embodiment depicted in FIG. 8, the docking station 20 includes a further temperature sensor 310 positioned adjacent to the needle 108 of the cartridge 100. The temperature sensor 310 can detect a temperature of the needle 108 and provide the temperature reading to the control module of the docking station 20. Thus, control module can be configured to take into account the temperature of the needle 108 when controlling the power supply to the coils 310.

As shown in FIG. 8, a positioning sleeve 400 is positioned within the slot 302 so as to substantially surround the application device 10. The positioning sleeve 400 can be removed from the slot 302 and sterilized, for example, in an autoclave. The positioning sleeve 400 therefore makes the system more hygienic. To facilitate sterilization, the positioning sleeve 400 can be made from a polymeric material, such as nylon.

Figure 9A:
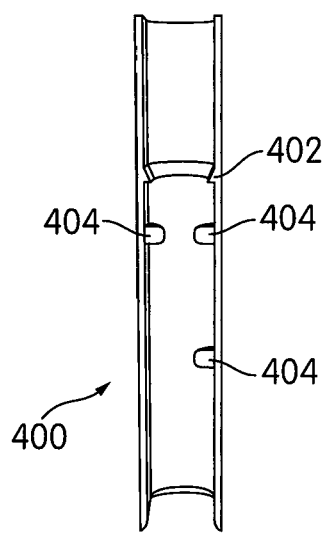
FIGS. 9(A) and 9(B) are views of a docking sleeve according to an embodiment of the invention.
Figure 9B:
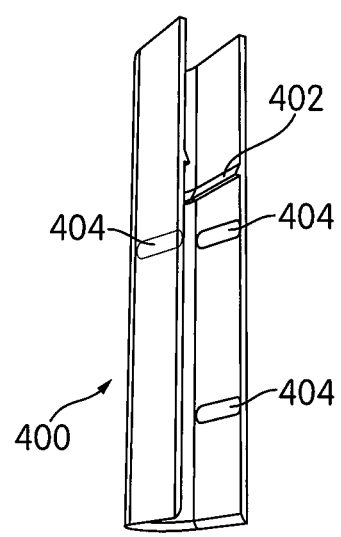

Details of the positioning sleeve 400 are shown in FIGS. 9(A) and 9(B). In the depicted embodiment, the positioning sleeve 400 has a U-shape. This shape facilitates cleaning of the positioning sleeve 400 by making the inside of the sleeve 400 easily accessible. The shape of the sleeve 400 can also serve an indication of the proper orientation of the sleeve 400 relative to the docking station 10 when the sleeve 400 is being inserted into a slot 302. The positioning sleeve 400 includes a notch 402 toward the inside of the sleeve 400. As shown in FIG. 8, the notch 402 corresponds to a flared part 120 of the sleeve 102 of the cartridge 100 when the application device 10 is inserted to the slot 302. As such, the notch 402 functions to correctly position the application device 10 within the slot 302. The positioning sleeve 400 also includes slots 404 that correspond to the positions of the temperature sensors 306, 308, and 310 when the positioning sleeve 400 is provided in the slot 302. The cartridge 100 is thereby visible to the temperatures sensors 306, 308, and 310 through the slots 404.

As will be appreciated by those skilled in the art, different endodontic materials have different heating requirements in order to achieve viscosities that allow the endodontic material to easily flow out of the application device 10. For example, generally speaking, gutta percha may be sufficiently softened at temperatures ranging from 90° C. to 125° C. Further, needles used with the application device 10 can come in different gauges (i.e., sizes) that will affect how easily the endodontic material can flow through the needles. With such factors in mind, in order to ensure that a proper amount of inductive heating of the endodontic material is provided with the system according to the invention, a coding system may be provided with each cartridge 100 and the docking station 20. As an example of such a system, a cartridge 100 may be color coded based on the particular endodontic material contained in the cartridge 100 and the particular needle 108 gauge of the cartridge 100. The color code can be provided on a surface of the cartridge 100 that is visible to an optical sensor that is provided in the docking station 20 (the optical sensor being similar to the optical sensors used for temperature detection provided above). The optical sensor can thereby read the color code from the cartridge and provide an indication to the user of how the docking station 10 should be operated for proper inductive heating of the particular cartridge. In this regard, the docking station 10 may have a control buttons 312, one of which is made to light up when the optical sensor determines the color code for the particular cartridge 100. The operator can thereby push one of the buttons 312 that will initiate a correct heating cycle in the docking station 10 for the particular cartridge.

Those skilled in the art will also recognize numerous possible variations to the particular temperature coding system described above. For example, as an alternative to using a sensor within the docking station 10 to determine the color code of the cartridges, the color coding provided on the cartridges can be made easily visible to the user, and the buttons on the docking station 10 can made in colors corresponding to the color coding provided on the cartridges. Thus, the operator may simply view the color coded on a cartridge, and then push the corresponding button to select the correct heating cycle for the cartridge. As another example, as an alternative to the user selecting the heating cycle for a cartridge, the control module of the docking station 10 could be programed to automatically select the correct heating cycle after the code for a particular cartridge 100 is detected by a sensor in the docking station 10. Further, there are various alternatives to using color for coding the heating cycles. For example, an alpha/numeric code (e.g., a bar code) could be provided on the cartridges, with the alpha/numeric code being detected by a sensor in the docking station 10.

With the invention described herein, systems for providing an endodontic material can be provided, with the systems using induction heating to heat cartridges containing the endodontic material. Because the systems use induction heating, no electrical heating parts need to be provided to the application devices including the cartridges. Moreover, with the induction heating the cartridges can quickly and efficiently be heated. Still further, the systems are easily adaptable for cartridges having different heating requirements.

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supportable by this application and the equivalents thereof, rather than by the foregoing description.

INDUSTRIAL APPLICABILITY

The systems described herein can be used for commercial products for use in dental procedures, such as devices used in endodontics. The systems described herein therefore clearly have industrial applicability.

The invention claimed is:

1. A system for providing endodontic material, the system comprising:
   (i) an application device comprising:
      (A) a cartridge including (a) a chamber structure containing endodontic material and (b) an outer sleeve having a flared part at one end of the outer sleeve; the outer sleeve configured to surround at least part of the chamber structure; and
      (B) a handle assembly configured to hold the cartridge; wherein the chamber structure is spaced from the outer sleeve by spacer pegs that extend between an outer surface of the chamber structure and an inner surface of the outer sleeve such that an air gap is formed between the outer surface of the chamber structure and the outer sleeve; wherein the chamber structure is formed from a ferromagnetic metal alloy material such that chamber structure is capable of being heated by magnetic induction, and
   (ii) a docking station including (a) a slot configured to contain the application device with a part of the application device being positioned in the slot, (b) at least one optical sensor facing the outer sleeve of the cartridge in order to detect a temperature of the cartridge of the application device, the docking station being provided with at least one induction heating coil positioned adjacent to the slot.

2. The system according to claim 1, wherein the docking station includes one induction heating coil positioned adjacent to a first side of the slot and a second induction heating coil positioned adjacent to a second side of the slot that is opposite to the first side.

3. The system according to claim 1, further comprising: a positioning sleeve configured to be placed between at least a part of the slot and the application device, with the sleeve being removable from the docking station.

4. The system according to claim 3,
   wherein the positioning sleeve is a vertical U-shaped body that includes an inward facing surface comprising (i) a notch in the inward facing surface of the sleeve, located at an upper one-third of a total length of the positioning sleeve that corresponds to the flared part of the outer sleeve of the cartridge when the application device is inserted into the slot of the docking station; and (ii) at least one slot located in a remaining bottom two-third of the total length of the positioning sleeve that correspond to a position of at least one optical sensor when the positioning sleeve is provided in the slot of the docking station; and wherein the cartridge is visible to the at least one optical sensor through the at least one slot of the positioning sleeve.

5. The system according to claim 1, wherein the docking station includes a control module operatively connected to the heating coil, with the control module being configured to cause the induction heating coil to operate in one of multiple heating cycles.

6. The system according to claim 5, wherein the docking station include a plurality of buttons operatively connected to the control module, and
   wherein the control module causes a particular heating cycle of the multiple heating cycles when one of the buttons is pressed.

7. The system according to claim 1, wherein the cartridge of the application device includes at least one coding structure that indicates at least one of a gauge of a needle provided with the cartridge and a heating requirement for the endodontic material contained in the cartridge, and
   wherein the docking station includes a sensor configured to detect the coding structure provided on the cartridge.

8. The system according to claim 1, wherein the endodontic material is gutta percha.

9. The system according to claim 1, wherein the outer sleeve including a slot extending through a wall of the outer sleeve that allows the outer surface of the chamber structure to be viewed from the outside of the outer sleeve.

10. The system according to claim 9, further comprising a thermo-activated strip positioned on the chamber structure, wherein the thermo-activated strip is visible through the slot from outside of the outer sleeve.

11. The system according to claim 9, further comprising a needle attached to an end of the chamber structure and extending from an end of the outer sleeve, the needle being in communication with the inside of the chamber structure such that the endodontic material may move from the inner chamber structure to the needle.

12. The system according to claim 1, wherein the at least one induction heating coil are positioned adjacent and at a distance to a both section of the cartridge with the chamber structure and a needle.

13. A system for providing endodontic material, the system comprising:
   (i) an application device comprising:
      (A) a cartridge including (a) a chamber structure containing endodontic material and (b) an outer sleeve having a flared part at one end of the outer sleeve; the outer sleeve configured to surround at least part of the chamber structure; and
      (B) a handle assembly configured to hold the cartridge;

wherein the chamber structure is spaced from the outer sleeve by spacer pegs that extend between an outer surface of the chamber structure and an inner surface of the outer sleeve such that an air gap is formed between the outer surface of the chamber structure and the outer sleeve; wherein the chamber structure is formed from a ferromagnetic metal alloy material such that chamber structure is capable of being heated by magnetic induction, and (ii) a docking station having a plurality of spaced apart slots, each slot configured to include the application device with a part of the application device being positioned in the slot, wherein the docking station includes one induction heating coil positioned adjacent to a first side of the slot and a second induction heating coil positioned adjacent to a second side of the slot that is opposite to the first side.

\* \* \* \* \*